United States Patent
Tsai et al.

(10) Patent No.: US 7,309,428 B2
(45) Date of Patent: Dec. 18, 2007

(54) APPARATUS FOR SEPARATING COMPONENTS FROM BLOOD PLASMA

(75) Inventors: Chen-Chi Tsai, Jhonghe (TW); Yung-Chih Wu, Yonghe (TW)

(73) Assignee: Industrial Technology Research Institute, Hsinchu (TW)

( * ) Notice: Subject to any disclaimer, the term of this patent is extended or adjusted under 35 U.S.C. 154(b) by 528 days.

(21) Appl. No.: 10/962,609

(22) Filed: Oct. 13, 2004

(65) Prior Publication Data

US 2005/0133447 A1    Jun. 23, 2005

(30) Foreign Application Priority Data

Dec. 23, 2003    (TW) .............................. 92136585 A

(51) Int. Cl.
*B01D 61/18*    (2006.01)
*B01D 63/00*    (2006.01)

(52) U.S. Cl. ................. 210/257.2; 210/198.1; 210/209; 210/252; 210/257.1; 210/258; 210/321.6; 210/416.1; 210/424; 210/483; 210/488; 210/489; 210/500.21; 210/500.29; 210/500.41; 422/101; 422/103

(58) Field of Classification Search ............... 210/102, 210/109, 143, 195.1, 198.1, 209, 252, 257.1, 210/257.2, 258, 321.6, 321.75, 321.84, 416.1, 210/424, 453, 473, 477, 483, 488, 489, 500.21, 210/500.22, 500.29, 500.41; 422/101, 103, 422/946; 435/2

See application file for complete search history.

(56) References Cited

U.S. PATENT DOCUMENTS

| 6,197,194 | B1 * | 3/2001 | Whitmore ................ 210/321.8 |
| 6,274,090 | B1 * | 8/2001 | Coelho et al. ............... 422/101 |
| 6,905,612 | B2 * | 6/2005 | Dorian et al. ................ 210/806 |
| 2005/0205498 | A1 * | 9/2005 | Sowemimo-Coker et al. ... 210/782 |

* cited by examiner

*Primary Examiner*—John Kim
(74) *Attorney, Agent, or Firm*—Bacon & Thomas PLLC

(57) ABSTRACT

The present invention relates to a process and apparatus for separating blood plasma, having a mixing unit in the form of a first injection having a first connecting tube and a first piston to provide a compartment for a mixture composed of plasma to be separated and the protein-precipitating agent; a separating unit composed of a filtering tube for separating and preserving a solid material after separation. The filtering tube includes a third connecting tube a filter and a third piston, the third connecting tube communicates with the fourth injection tube having a fourth piston for receiving a separated liquid; and a storage unit in the form of a fifth injection tube having a fifth connecting tube, a second connecting valve and a fifth piston.

11 Claims, 4 Drawing Sheets

APPARATUS FOR SEPARATING COMPONENTS FROM BLOOD PLASMA

BACKGROUND OF THE INVENTION

1. Field of the Invention

The present invention relates to a process and apparatus for separating components from blood plasma, and more particularly to a process and apparatus suitable for speedily separating thrombin, fibrinogen and Factor X III from blood plasma.

2. Description of Related Art

Human blood plasma is the yellow, protein-rich fluid that suspends the cellular components of whole blood, that is, the red blood cells, white blood cells and platelets. Plasma, which is 90 percent water, constitutes about 55 percent of the total blood volume. Plasma contains albumin (the chief protein constituent), fibrinogen (responsible, in part, for the clotting of blood), globulins (including antibodies) and other clotting proteins. Plasma serves a variety of functions, from maintaining a satisfactory blood pressure and providing volume to supplying critical proteins for blood clotting and immunity. Plasma is obtained by separating the liquid portion of blood from the cells suspended therein.

Much the same as crude oil is broken down into its component parts, blood plasma, once separated from the other components of whole blood, can be further separated into a number of valuable plasma components. Some of these plasma components, such as fibrinogen and thrombin, are very valuable. The process by which plasma is separated into some of its different component parts is known as fractionation.

Conventionally, the method for separating the desired proteins is generally achieved by protein precipitation. The common methods for precipitating proteins are as follow: (a) Ammonium sulfate precipitation method: Certain proportions of non-polar regions are distributed over the surfaces of every protein molecule. The non-polar regions accumulate a number of water molecules to be dissolved into an aqueous solution. If a large amount of ammonium sulfate is added into the aqueous solution, the water molecules, which accumulate over the surfaces of protein, will be removed because of the capability of high hydration of ammonium sulfate. As such, the non-polar regions on the surfaces of protein are exposed, and then, protein complexes are precipitated by an affinity for the hydrophobic surfaces of the protein. (b) Isoelectric point precipitation method: If the pH of a protein solution is adjusted to its isoelectric point, the net charge of the protein will be zero. Thus, the repulsion between molecules decreases so that protein complexes are precipitated because of self-interaction of these molecules. (c) Organic solvent precipitation method: The concentration of water molecules is diluted by addition of a large amount of an organic solvent into a protein solution. Thus, the solubility of protein decreases rapidly and a precipitation occurs Centrifugation is the most convenient method for liquid-solid separation. Hence, after the proteins are precipitated by the above-mentioned methods, the proteins in a solid state or a quasi-solid state are separated by centrifugation. The centrifugation is processed at a low temperature to prevent denaturation of the proteins at a high temperature while centrifugation is carried out.

The separating plasma components by a centrifuge and then transporting the product to the operation room takes a significant mount of time and as a result of no centrifuge equipment is provided in the operation room while in clinical use. Furthermore, the risks of plasma contamination will be increased during the transportation. Therefore, there is a need to provide a process and an apparatus that are capable of separating the different components of blood plasma for clinical use.

SUMMARY OF THE INVENTION

A primary object of the present invention is to provide an apparatus and a process for separating components from blood plasma so as to separate them in real time and reduce the possibility of being contaminated due to transportation of blood plasma for the separation.

Another object of the present invention is to provide an apparatus and a process for separation of components from blood plasma so as to prepare valuable plasma components immediately at the time of surgery so that autologous blood can be utilized.

To attain the aforesaid objects, an apparatus for separating components from blood plasma according to the present invention comprises a mixing unit in the form of a first injection tube into which a protein-precipitating agent is filled, the first injection tube having a first connecting tube and a first piston, in which a compartment is formed for a mixture composed of the blood plasma to be separated and the protein-precipitating agent; a separating unit composed of a filtering tube for separating the mixture supplied from the mixing unit and preserving a solid material generated after the separation, and a fourth injection tube is for receiving a liquid after the separation, the filtering tube including a third connecting tube, a filter and a third piston and communicates with the fourth injection tube; and a storage unit in the form of a fifth injection tube having a fifth connecting tube, a second connecting valve and a fifth piston to accommodate a liquor to dissolve the solid material as a result of the separation; wherein the first connecting tube is connected to the first injection tube and the filtering tube, the fifth connecting tube is connected to the third connecting tube, and the second connecting valve is positioned at the interconnection of the third connecting tube and the fifth connecting tube to control the flow direction of fluid in the separating unit and the storage unit.

In the apparatus for separating components from blood plasma according to the present invention, the mixing unit further comprises a second injection tube having a second connecting tube, a first connecting valve and a second piston to accommodate the plasma to be separated, where the second connecting tube is connected to the first connecting tube and the first connecting valve is positioned at the interconnection of the first connecting tube and the second connecting tube to control the flow direction of fluid in the mixing unit and the separating unit.

The present invention further provides a process for separating components from blood plasma comprising the steps of: (a) providing a mixing unit, a filtering unit and a storage unit, wherein the mixing unit is a first injection tube filled with a protein-precipitating agent, the first injection tube having a first connecting tube and a first piston to provide a compartment for a mixed liquid composed of plasma to be separated and the protein-precipitating agent; the separating unit is composed of a filtering tube and a fourth injection tube, the filtering tube including a third connecting tube, a filter and a third piston, and the fourth injection tube including a fourth piston; and the storage unit is a fifth injection tube including a fifth connecting tube, a second connecting valve and a fifth piston; (b) connecting the first connecting tube with the first injection tube and the filtering tube, the third connecting tube connecting with the filtering tube and the fourth injection tube, and the fifth connecting tube connecting with the third connecting tube, wherein the second connecting valve is positioned at the interconnection of two of the connecting tubes to control the flow direction of fluid in the separating unit and the storage unit; (c) infusing the mixture in the mixed unit into the filtering tube of the separating unit, and a solid material is left in the filtering tube while a liquid is collected in the fourth injection tube; and (d) dissolving the solid material in the filtering tube with a liquor to form a solution. In the process according to the present invention, a step (e), pushing the solution into the fifth injection tube for being kept in reserve, is included, subsequent to step (d).

In the apparatus and the process for separating components from blood plasma according to the present invention, the protein-precipitating agent is not specifically defined, preferably ammonium sulfate, ethanol or polyethylene glycol (PEG).

The present invention can be used for purifying fibrinogen and Factor X III from blood plasma, or thrombin from the supernatant after removed of fibrinogen and Factor X III. In addition, thrombin was purified after the supernatant without fibrinogen and Factor X III was mixed with calcium buffer. The calcium buffer is not specifically defined, preferably, buffers with calcium ion, calcium chloride, calcium carbonate or calcium hydroxide.

The filter material in the filtering tube of the present invention is not specifically defined. Preferably, the filter is made of a sponge-like material. The pore size of the filter is not specifically defined, preferably in the range of 200 to 1,000 μm. A filtration membrane is further provided below the filter in the filtering tube to collect tiny precipitates. The pore size of the filtration membrane is not specifically defined, preferably in the range of 3 to 10 μm. The material of the filtration membrane is not specifically defined, being a conventional one. Preferably, the filtration membrane is made of cellulose ester or polysulfone. The filter membrane of the present invention is a cellulose filter—filter paper No. 9.

The liquor used in the present invention to dissolve the solid material after separation is not specifically defined, preferably water, calcium chloride solution or neutral buffer solution. The first connection valve and the second connecting valve in an apparatus according to the present invention is not specifically defined and featured. Preferably, the valve is a three-way valve. An automatic control unit can be further connected to the present invention apparatus for automatic control.

In the process according to the present invention, the source for supplying the liquor used in step (d) is not specifically defined, and also, it can be externally added directly into the filtering tube. Preferably, the liquor is infused by the fifth injection tube to dissolve the solid material in the filtering tube.

The mixing unit, the separating unit and the storage unit used in an apparatus according to the present invention are not specifically graded. Preferably, those units are made for medical use, having been subjected to an aseptic process. Moreover, all the processing steps are operated under an aseptic environment.

Other objects, advantages, and novel features of the invention will become more apparent from the following detailed description when taken in conjunction with the accompanying drawings.

DETAILED DESCRIPTION OF THE PREFERRED EXAMPLES

Preferred examples of the present invention will now be described to illustrate the technical contents involved in the present invention.

Example 1

Figure 1:
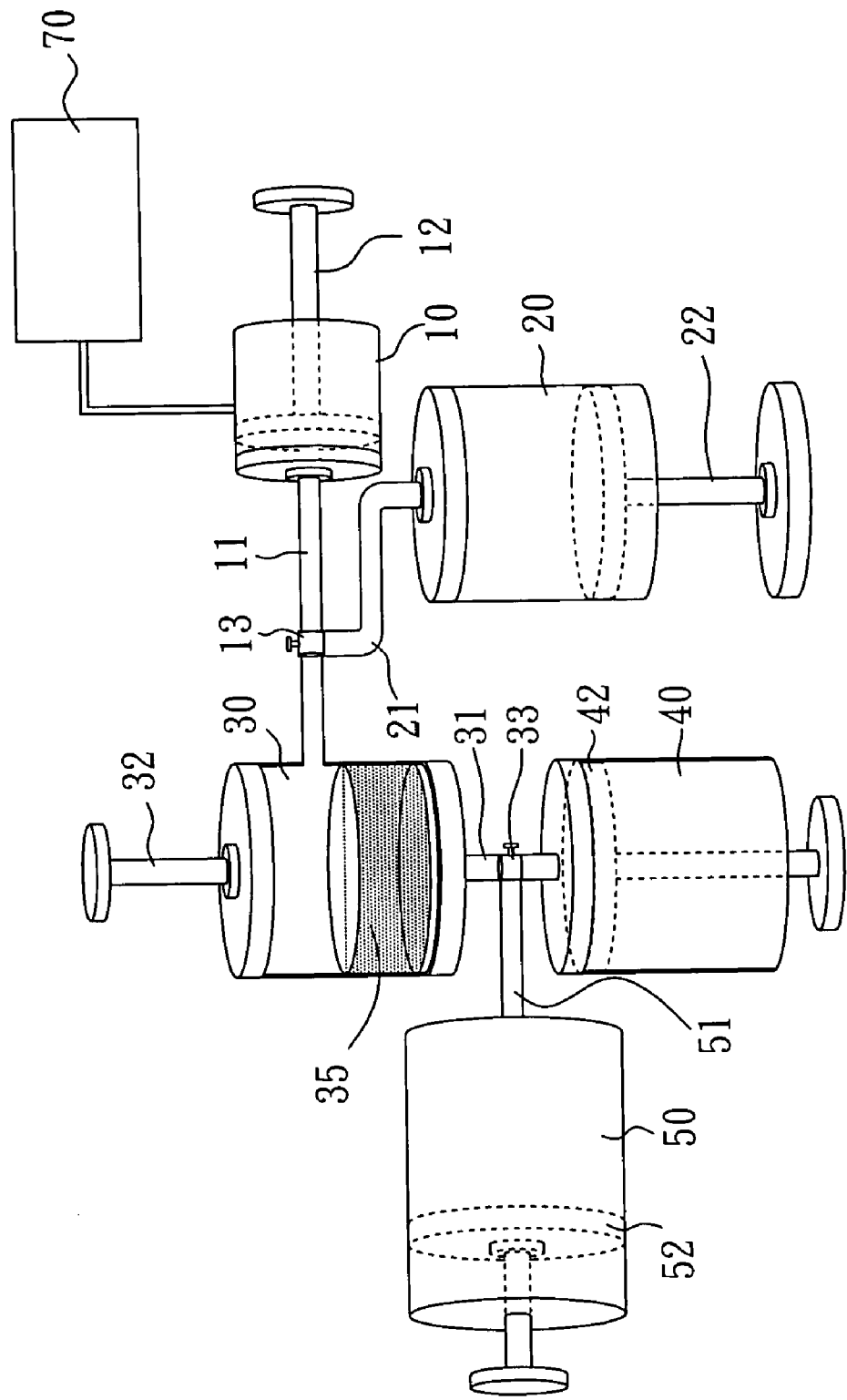
FIG. 1 is a structural diagram of a preferred example according to the present invention.

Referring to FIG. 1, an apparatus for separating components from blood plasma according to the present invention comprises a mixing unit in the form of a first injection tube 10 and a second injection tube 20, a separating unit in the form of a filtering tube 30 and a fourth injecting tube 40, and a storage unit in the form of a fifth injection tube 50.

The first injection tube 10 has a first connecting tube 11 connected to the first injection tube 10 and the filtering tube 30. The second injection tube 20 has a second connecting tube 21 connected to the first connecting tube 11. A first connecting valve 13 is mounted at the interconnection between the first connecting tube 11 and the second connecting tube 21. In this example, the first connecting valve 13 is a three-way valve to control the flow direction of fluid inside the first connecting tube 11 and the second connecting tube 21.

The filtering tube 30 has a third connecting tube 31 for connecting the filtering tube 30 with the fourth injection tube 40. The fifth injection tube 50 has a fifth connecting tube 51 for connecting up the third connecting tube 31. A second connecting valve 33 is mounted at the interconnection between the fifth connecting tube 51 and the third connecting tube 31. In this example, the second connecting valve 33 is a three-way valve to control the flow direction of fluid inside the fifth connecting tube 51 and the third connecting tube 31.

In this example, the first injection tube 10 comprises a first piston 12 to be filled with a protein-precipitating agent (PEG or ammonium sulfate), in addition to the first connecting tube 11. The first piston 12 is then used to control the release of the protein-precipitating agent in the first injection tube 10.

In this example, the filtering tube 30 comprises a third piston 32 and a filter 35, in addition to the third connecting tube 31. The filter adopted in this example is a porous sponge used for hemodialysis in medical use. When the third piston 32 is pumped, a mixture in the filtering tube 30 flows through the filter 35 to fulfill the separation. In this example, the mixture in the filtering tube 30 results from mixing the blood plasma with the precipitating agent supplied by the second injection tube 20.

Similarly, the fourth injection tube 40 has a fourth piston 42. Because the fourth injection tube 40 is connected up with the filtering tube 30, separation of the mixture left in the filtering tube 30 is processed with the filter 35 by slowly drawing the fourth piston 42 out or pumping the third piston 32 in the filtering tube 30 to bring about a filtered liquid to be filled into the fourth injection tube 40 and a solid precipitate left on the filter.

In this example, the fifth injection tube 50 comprises a fifth piston 52. A liquor (such as water in this example) in the fifth injection tube 50 is infused to the filtering tube 30 in cooperation with pumping movements of the fifth piston 52. Thus, the precipitate left in the filtering tube 30 is dissolved. In this example, the precipitate is solid, and comprises fibrinogen and Factor X III.

An automatic control unit 70 is included in this example to facilitate an automatic control of all the injection tubes and components to complete the separating procedures.

Example 2

The present example is used to illustrate a process for separating components form blood plasma according to the present invention.

At the beginning, the injection tubes (the first injection tube 10, the second injection tube 20, the filtering tube 30, the fourth injection tube 40 and the fifth injection tube 50) and components (connecting tubes 11, 31, 51 and three-way valves 13, 33) are assembled as described in example 1. A precipitating agent—4.5 ml of 30% polyethylene glycol (PolyScience Inc.) or 3 ml saturated ammonium sulfate (Sigma) is filled into the first injection tube 10. 9 ml of blood plasma to be separated is infused into the second injection tube 20. Take 1.5 ml of water for dissolving a precipitate of blood plasma is infused into the fifth injection tube 50.

The three-way valve 13 is adjusted so that the first injection tube 10 communicates with the second injection tube 20. The first piston 12 is pumped to infuse the precipitating agent from the first injection tube 10 into the second injection tube 20 through the first connecting tube 11 and the second connecting tube 21. The precipitating agent is mixed with the blood plasma in the second injection tube 20. The mixture contains a solid precipitate and a liquid. Then, the three-way valve 13 is adjusted so that the second injection tube 20 communicates with the filtering tube 30. The second piston 22 is pumped to infuse the mixture from the second injection tube 20 into the filtering tube 30.

The three-way valve 33 is adjusted to communicate the filtering tube 30 and the fourth injection tube 40. The third piston 32 is then pumped to separate the mixture by filtering. The fourth piston 42 is slowly drawn out to filter a liquid flow into the fourth injection tube 40. The filtrate (or the supernatant) obtained from the fourth injection tube 40 is kept for further purification for thrombin.

The solid precipitate after filtration is left in the filtering tube 30. The three-way valve 33 is adjusted to communicate the filtering tube 30 with the fifth injection tube 50. The fifth piston 52 is pumped to infuse water from the fifth injection tube 50 into the filtering tube 30. The solid precipitate in the filtering tube 30 is dissolved for about 20 to 30 minutes. Then, the fourth piston 42 is pumped to flow the dissolved solution from the filtering tube 30 into the fifth injection tube 50. Consequently, the separation of components in blood plasma is complete.

Example 3

Inspections of Separated Plasma Components Effects

The components separated from blood plasma according to the present apparatus and process will be inspected by the following tests for the quality thereof in respect of fibrinogen concentration and gel-clot assay.

(a) Test for Fibrinogen Concentration

The formulas and processing steps for quantitatively determining fibrinogen concentration by sodium dodecyl sulfate polyacrylamide gel electrophoresis (SDS-PAGE) are as follow.

1. A 9% separating gel: 0.375 molar (M) Tris-HCl at pH 8.8, 0.1% SDS, 9% acrylamide/bis (30:0.8), 0.075% ammonium persulfate (APS), and 0.05% N,N,N',N'-tetramethylethylenediamine (TEMED).
2. A 5% stacking gel: 0.125M Tris-HCl at pH 6.8, 0.1% SDS; 5% acrylamide/bis (30:0.8), and 0.075% APS; 0.075% TEMED.
3. A running buffer:25 mM Tris, 192 mM glycine, and 0.1% SDS.
4. The products separated in example 2 are loaded into gel, and electrophoresis is processed in a tank at a voltage of 150V for about 110 minutes.
5. Protein staining: Staining is processed for 40 minutes in a solution (0.2% coomassie brilliant blue G-250), 50% methyl alcohol, and 7% acetic acid) after the electrophoresis is complete.
6. A destaining is processed in a solution (50% methyl alcohol and 7% acetic acid) after staining.
7. The gel after destaining is dried in the shade, and then, a quantitative analysis is processed by computer software. The concentration of the protein is analyzed by linear regression.

Figure 2A:
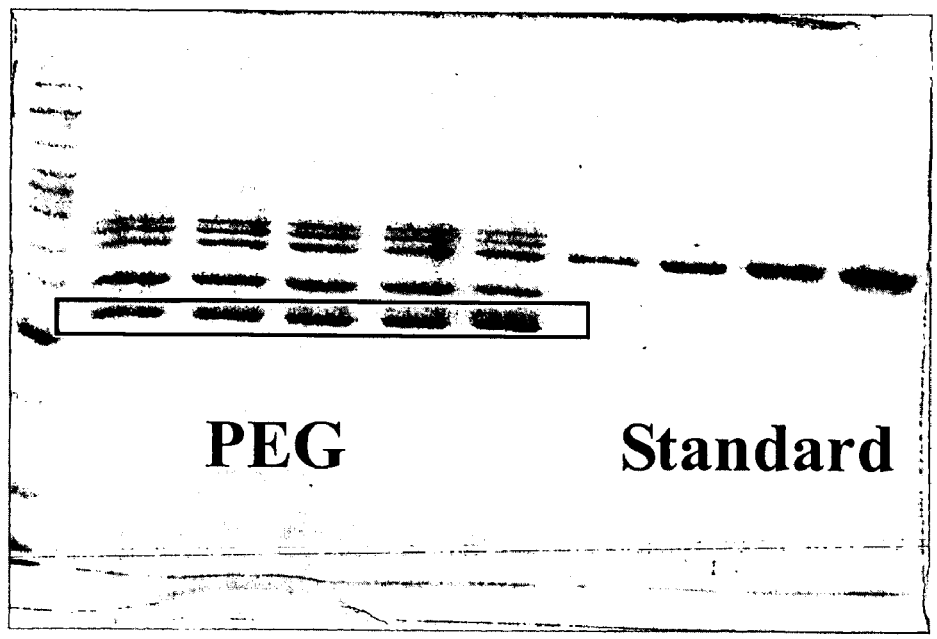
FIG. 2a is an electrophoresis result of fibrinogen precipitated with polyethylene glycol.
Figure 2B:
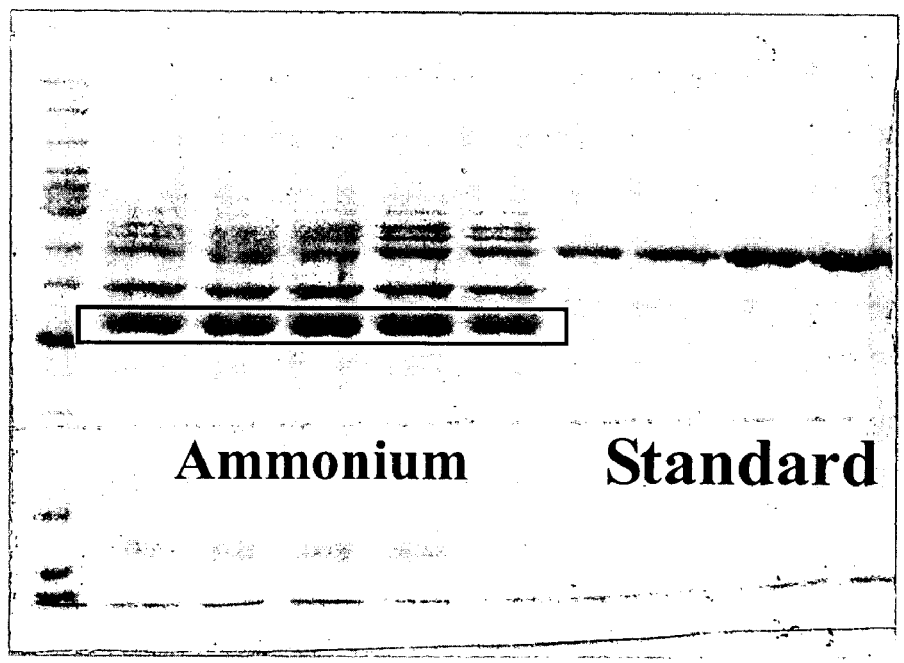
FIG. 2b is an electrophoresis result of fibrinogen precipitated with ammonium sulfate.

The experimental results of dissolved samples after separation with different precipitating agents are shown in FIGS. 2a and 2b, respectively, where FIG. 2a shows precipitation with polyethylene glycol while FIG. 2b shows precipitation with ammonium sulfate. In these figures, the rectangular frames indicate the amount of fibrinogen contained in the dissolved samples after separation, and the concentration of fibrinogen being capable of reaching 10.4 mg/ml.

(b) Gel-Clot Assay

Figure 3A:
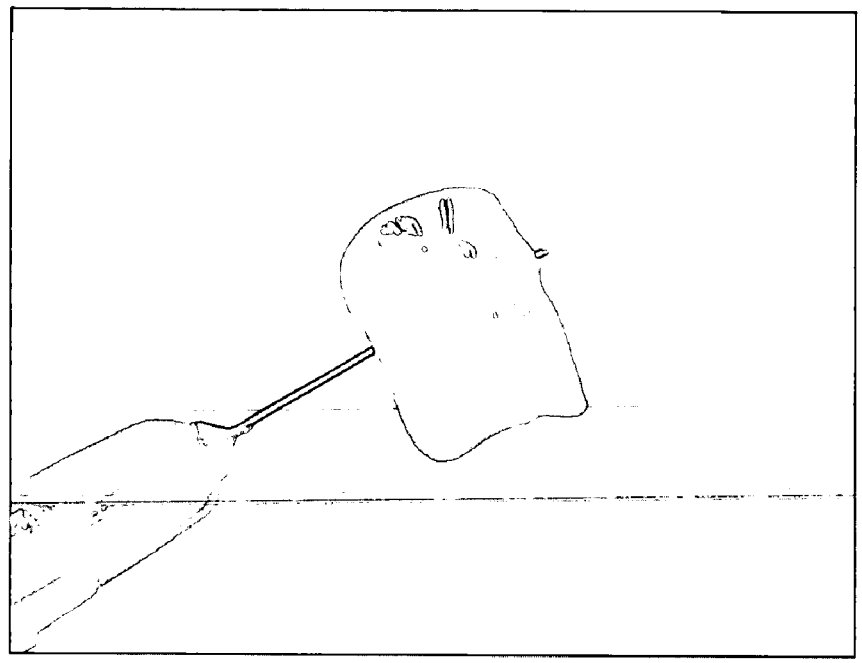
FIG. 3a is a result of a solution separated in accordance with the present invention under a gel-clot assay.
Figure 3B:
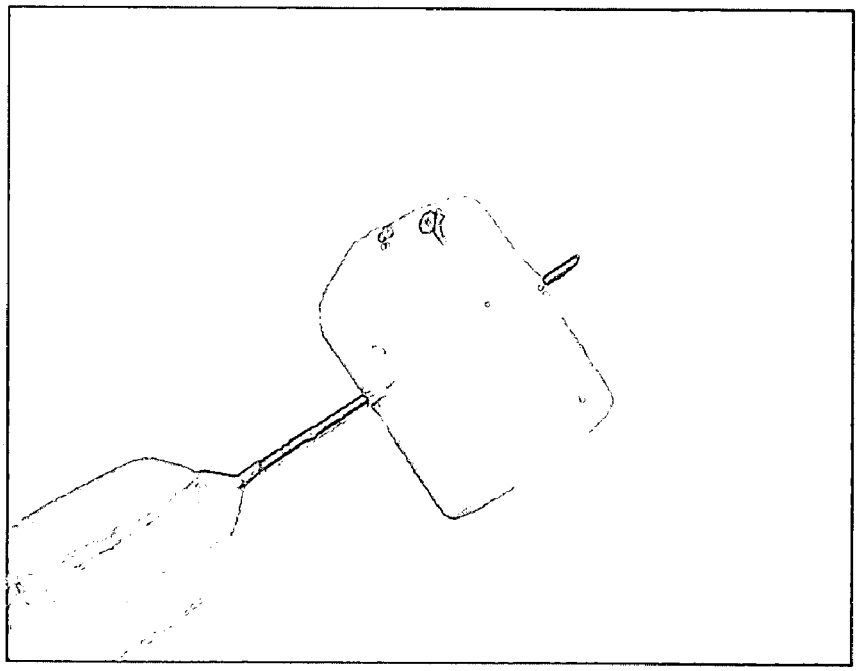
FIG. 3b is another result of a solution separated in accordance with the present invention under a gel-clot assay.

Fibrinogen produced in example 2 is mixed with collagen with different concentrations for gel-clot assay. The results of different gel-clot assays are shown in FIGS. 3a and 3b. The ratio of fibrinogen to collagen in FIG. 3a is 1 to 2 while the ratio of fibrinogen to collagen in FIG. 3b is 5 to 1. It is clear from the gel-clot assays that the result separated with the apparatus and process in accordance with the present invention show an excellent gel-clotting effect.

The present invention is able to provide an apparatus and process for separating components from blood plasma and to prevent the plasma from being contaminated, and the resulting fibrinogen after separating from plasma also achieves an excellent gel-clotting effect.

Example 4

Purification of Thrombin

The supernatant obtained and kept in the fourth injection tube 40 in example 2 was taken to perform further extraction of thrombin. The supernatant was added with calcium solution (preferably, calcium chloride) until the final concentration of the calcium reached 0.1M. The solution mixed with calcium was shaken mildly for 10-30 minutes. Then the mixed and reacted solution was transferred into the second injection tube 20. Then the mixed solution was purified through the purification steps as described in example 2

Example 5

Estimated the Activity of Thrombin Purified from Example 4

Standard solutions of various concentrations (0.05, 0.1, 0.2, 0.5, 0.8, 1 unit/ml) were prepared by diluting thrombin (Sigma) with solution A (50 mM Tris-HCl, 0.1M NaCl, 0.05% BSA, pH 7.4). Then the product obtained in example 4 was diluted in 200 times with solution A, too. The substrate (S-2238, from Chromogenix) of thrombin was also diluted to 0.3 mg/ml with solution B (50 mM Tris-HCl, 0.1M NaCl, pH 7.4). Then 50 µl of standard solutions, 50 µl of sample solutions and 50 µl of substrate were added into wells of a 96-well plate. The reaction mixture of each well was kept intact for 3 minutes and the reactions were quenched with 205 acetic acid. The results were assayed with an ELISA reader under 405 nm.

Figure 4A:
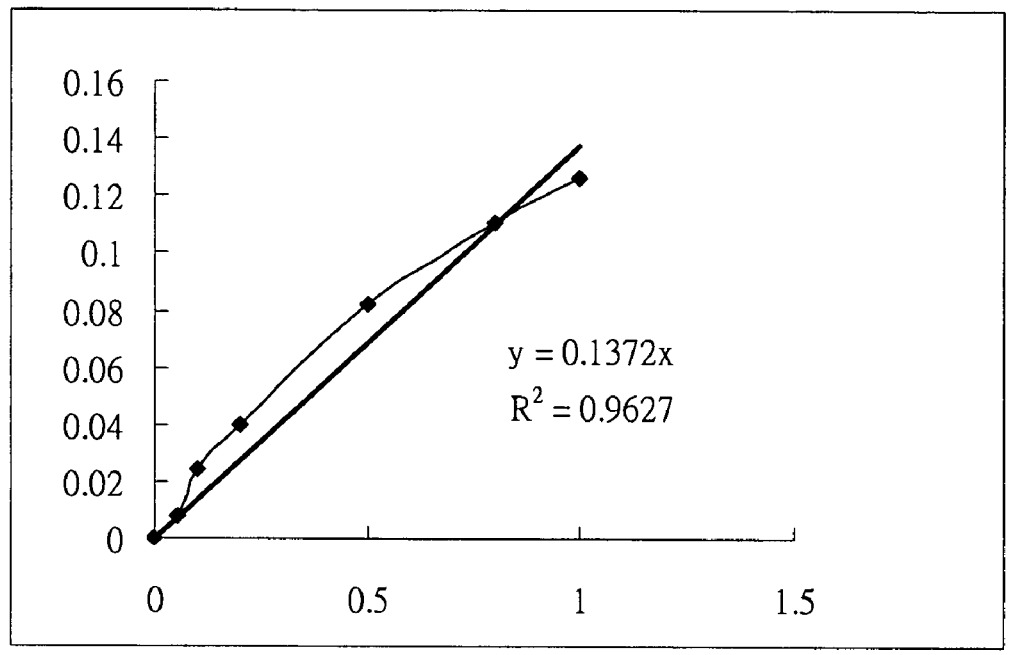
FIG. 4a is a figure of standard curve of thrombin activity.

According to the results shown in FIG. 4a, the curve of thrombin activity of the precipitate after re-dissolved with 1 ml $CaCl_2$ shows high activity (174±3.82 unit/ml). Obviously, the product re-dissolved with less $CaCl_2$, could obtain higher activity of thrombin.

The gel forming ability of the purified thrombin was evaluated subsequently. The thrombin purified by the process illustrated above with various volumes of 30% polyethylene glycol (1 ml, 2 ml, 3 ml, 4 ml, and 5 ml) was mixed with fibrinogen or thrombosis factor to evaluate the gel forming ability. The result is shown in FIG. 4b.

Figure 4B:
FIG. 4b is a result of gel forming ability after purification with various ratios of polyethylene glycol.

According to FIG. 4b, A-E drops show the gel forming ability of products purified with different ratio of 30% polyethylene glycol (i.e. A: 1 ml, B: 2 ml, C: 3 ml, D: 4 ml and E: 5 ml). All the products purified with various ratios of polyethylene glycol show a good gel forming ability.

The present invention intends to cover various modifications and similar arrangements obvious to a person skilled in this art. The scope of the claims, therefore, should be accorded the broadest interpretation so as to encompass all such modifications and similar arrangements.

What is claimed is:

1. An apparatus for separating components from blood plasma, comprising:

a mixing unit in the form of a first injection tube containing a protein-precipitating agent, said first injection tube having a first connecting tube and a first piston to provide a compartment for a mixture composed of plasma to be separated and said protein-precipitating agent;

a separating unit composed of a filtering tube, a third connecting tube, a filter in said filtering tube, and a third piston, for separating said mixture supplied from said mixing unit and preserving a solid material after said separation, said third connecting tube communicates with a fourth injection tube having a fourth piston for receiving a liquid after said separation; and a storage unit in the form of a fifth injection tube having a fifth connecting tube, a second connecting valve and a fifth piston and containing a liquor to dissolve said solid material in said filtering tube as a result of said separation;

wherein said first connecting tube is connected to said first injection tube and said filtering tube, said fifth connecting tube is connected to said third connecting tube, and said second connecting valve is positioned at an interconnection of said third connecting tube and said fifth connecting tube to control a flow direction of fluid in said separating unit and said storage unit.

2. The apparatus of claim 1, wherein said mixing unit further comprises a second injection tube having a second connecting tube, a first connecting valve and a second piston containing said plasma to be separated, said second connecting tube is connected to said first connecting tube, and said first connecting valve is positioned at the interconnection of said first connecting tube and said second connecting tube to control the flow direction of fluid in said mixing unit and said separating unit.

3. The apparatus of claim 2, wherein said first connecting valve is a three-way valve.

4. The apparatus of claim 1, wherein said second connecting valve is a three-way valve.

5. The apparatus of claim 1, wherein said protein-precipitating agent is ammonium sulfate, ethanol or polyethylene glycol (PEG).

6. The apparatus of claim 1, wherein said filter in said filtering tube is made of a sponge-like material.

7. The apparatus of claim 6, wherein said filter in said filtering tube has a pore size in the range of 200 µm to 1,000 µm.

8. The apparatus of claim 7, wherein a filtration membrane is further provided below said filter in said filtering tube to collect tiny precipitates.

9. The apparatus of claim 8, wherein said filtration membrane has a pore size in the range of 3 µm to 10 µm.

10. The apparatus of claim 9, wherein said filtration membrane is made of cellulose ester or polysulfone.

11. The apparatus of claim 1, wherein said liquor is water, calcium chloride solution or a neutral buffer solution.

* * * * *